United States Patent
Schenkl et al.

(10) Patent No.: US 6,771,373 B2
(45) Date of Patent: Aug. 3, 2004

(54) TURBIDITY SENSOR WITH TEMPERATURE SENSING FOR HOUSEHOLD APPLIANCES

(75) Inventors: Johann Schenkl, Bodenwöhr (DE); Georg Wilhelm, Guteneck (DE)

(73) Assignee: Elektromanufaktur Zangenstein Hanauer GmbH & Co. KGaA, Nabburg (DE)

(*) Notice: Subject to any disclaimer, the term of this patent is extended or adjusted under 35 U.S.C. 154(b) by 100 days.

(21) Appl. No.: 10/109,181

(22) Filed: Mar. 28, 2002

(65) Prior Publication Data

US 2003/0142316 A1 Jul. 31, 2003

(30) Foreign Application Priority Data

Jan. 31, 2002 (EP) ............................................. 02001933

(51) Int. Cl.[7] ............................................. G01N 21/00
(52) U.S. Cl. ....................................... 356/442; 356/72
(58) Field of Search ..................... 356/72–73, 441–442; 68/12.02; 134/58 D

(56) References Cited

U.S. PATENT DOCUMENTS

| | | | | |
|---|---|---|---|---|
| 4,257,708 A | * | 3/1981 | Fukuda | 356/442 |
| 4,463,572 A | * | 8/1984 | Brown, Jr. | 62/135 |
| 5,082,367 A | * | 1/1992 | Kohler et al. | 356/73 |
| 5,331,177 A | * | 7/1994 | Kubisiak et al. | 250/574 |
| 5,596,408 A | * | 1/1997 | Cummins et al. | 356/440 |
| RE35,566 E | * | 7/1997 | Boyer et al. | 356/72 |
| 5,923,433 A | * | 7/1999 | Giuffre et al. | 356/440 |
| 6,118,914 A | * | 9/2000 | Davis et al. | 385/37 |

FOREIGN PATENT DOCUMENTS

| DE | 69511858 T2 | 1/2000 |
|---|---|---|
| DE | 19831688 C1 | 4/2000 |
| DE | 20022433 U1 | 9/2001 |

* cited by examiner

Primary Examiner—Zandra Smith
Assistant Examiner—Kara Geisel
(74) Attorney, Agent, or Firm—Clifford W. Browning; Woodard, Emhardt, Moriarty, McNett & Henry LLP

(57) ABSTRACT

Sensor for household appliances, in particular washing machines and dishwashers, comprising a housing 2 which comprises first and second housing fingers 8, 10 extending from a basis, a first optical element 12 being arranged in the first housing finger 8, a second optical element 14 which is arranged in the second housing finger 10 wherein a sensing beam 16 transmitted and received by the optical elements 12, 14 is propagating between the housing fingers 8, 10 external to the housing 2 for sensing of the turbidity of a cleaning medium at least partially surrounding the housing 2, and a temperature sensor 18 which is arranged in the second housing finger 10 in a greater distance from the basis 4 compared to the second optical element 14 for sensing the temperature of the cleaning medium.

32 Claims, 1 Drawing Sheet

TURBIDITY SENSOR WITH TEMPERATURE SENSING FOR HOUSEHOLD APPLIANCES

FIELD OF THE INVENTION

Figure 1:
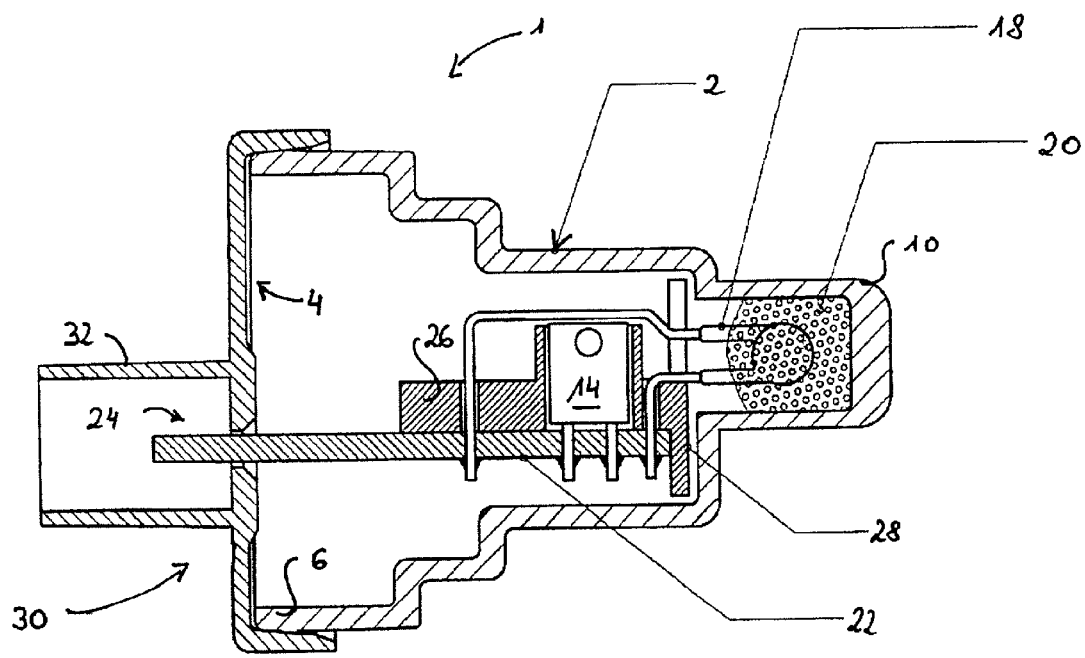

In general, the present invention relates to sensors for household appliances using cleaning media and, in particular, to sensors for sensing of the turbidity and temperature of cleaning media, e.g. used in washing machines and dishwashers.

BACKGROUND OF THE INVENTION

An essential feature of efficiency of a washing machine or a dishwasher is a low consumption of energy and water which essentially depends on the dirt level of products to be cleaned. Since the dirt level of a product to be cleaned can hardly be directly determined or can not be determined directly at all, it is known to employ so-called turbidity sensors to determine the dirt level of a product to be cleaned indirectly by means of the turbidity or dirtying of a cleaning medium.

By means of turbidity sensors, in general, utilizing a sensing beam propagating through a cleaning medium, the turbidity and dirtying, respectively, of the cleaning medium, for example cleaning or washing water, is determined. On the basis of the determined turbidity or dirtying of the cleaning medium, the current dirt level of the product to be cleaned is determined and the operation of a washing machine or a dishwasher is accordingly controlled to obtain an effective cleaning with a minimized consumption of energy and water.

Further, the effectiveness of the cleaning by means of a washing machine or a dishwasher depends from the temperature of the cleaning medium, since the temperature of the cleaning medium and, in particular, a temperature corresponding to a given temperature or a given temperature course corresponding to a given temperature course determines the removal of dirt particles from the product to be cleaned.

For that purpose, temperature sensors are employed which are arranged in the washing or cleaning area of a respective machine and sense the temperature of the cleaning medium. Further, temperature sensors shell ensure that the temperature of the cleaning medium does not exceed a value given for the product to be cleaned, in order, for example, not to damage pieces of clothes by too high temperatures during the washing.

Usually, washing machines or dishwashers are equipped with turbidity sensors and temperature sensors embodied as separate components which accomplish the respective measurements of the cleaning medium at different locations in the household appliance. This can lead to a non-effective operation, in particular in the case the turbidity values determined by a turbidity sensor and the temperature determined by a temperature sensor are combined to optimize the operation of the machine.

In addition, known sensors which determine the turbidity and the temperature of a cleaning medium of a washing machine or a dishwasher exhibit large sizes which occupy a respective area in the machine. Moreover, such sensors having large dimensions can distort the results of the measurements in the case, in the areas in the machine wherein the sensors are located, static and dynamic conditions of the cleaning medium result due to the sensor dimensions, which are different compared to the areas wherein the actual cleaning is performed.

A further problem of such combined sensors is that the components for a temperature registration are often distorted by the temperature generation from the sensors itself and/or temperature changes of cleaning medium are determined too slow because of its arrangement in the sensor.

OBJECT OF THE INVENTION

Object of the present invention is to overcome the above mentioned drawbacks of known solutions. In particular, the present invention shall provide a sensor for household appliances, such as washing machines or dishwashers, which determines fast and reliable both the turbidity and the temperature of a cleaning medium, has small dimensions and can be installed in a simple manner in a household appliance.

SHORT DESCRIPTION OF THE INVENTION

The object of the present invention is solved by a sensor which comprises a housing having two housing fingers extending from a basis. The both housing fingers, namely a first housing finger and a second housing finger are formed such that they are extending into a cleaning medium for the case of a sensor installed in a washing machine or a dishwasher.

In the first housing finger, a first optical element is arranged, while in the second housing finger, a second optical element is arranged.

For a measurement of the turbidity or dirtying of the cleaning medium, a sensing beam is employed which propagates between the optical elements from one housing finger to the other through the cleaning medium. Interactions of the sensing beam on its propagation path through the cleaning medium are employed to deduce the turbidity or dirtying of the cleaning medium.

Further, in the second housing finger, a temperature sensor for sensing the temperature of the cleaning medium is arranged such that the distance between the temperature sensor and the basis is larger than the distance between the second optical element and the basis.

In this manner, it is accomplished that the portion of the second housing finger wherein the temperature sensor is arranged is extending further into the cleaning medium compared to the portion of the second housing finger comprising the second optical element. This makes it possible to sense the temperature of the cleaning medium faster and more reliable since, for example, a heating of portions surrounding the temperature sensor or the temperature sensor itself by heat generating portions of the sensor is largely avoided.

The housing fingers can be designed such that the longitude axis thereof include an angle, wherein the distance between the free ends of the housing fingers can be larger or smaller than between the portions of the housing fingers which are connected to basis. In the case, the housing fingers are extending in a V-shape from the basis, a larger measuring path is obtained, even for an opposing arrangement of the first and second optical elements which enables for a more precise registration of the turbidity or dirtying of the cleaning medium.

To obtain a larger measuring path, it is further contemplated to arrange the first and second optical elements in a displaced manner in relation to the longitudinal axis of the housing fingers such that the measuring path between the optical elements is extending diagonally between the housing fingers. This extension of the measuring path is in particular suitable in the case where the first and second housing fingers are extending essentially parallel from the basis, which is why, in contrast to, for example, two housing fingers being arranged in a V-form, an essentially constant distance between the housing fingers is given.

Further, it is contemplated to arrange the first and second optical elements relatively to each other such that they lie on an axis which coincides with a straight propagation path for the sensing beam. Alternatively, is it possible to arrange the first and second optical elements relatively to such an axis in a displaced manner in order to register special interactions of the sensing beam on its propagation path through the cleaning medium (for example scattering effects).

To enable for more compact design of the sensor it, is contemplated that the first and second housing fingers have a different lengths wherein the second housing finger comprising the temperature sensor is longer than the other, first housing finger.

A reduced design can particularly be obtained in the case where the first optical element is arranged in an end portion of the first housing finger, i.e. in a portion of the first housing finger which is most remote from the basis.

Preferably, in the case of an utilization of housing fingers been different long, the temperature sensor is arranged as remote as possible from the basis, i.e. in an end portion of the second housing finger, wherein the second optical element is located between the temperature sensor and the basis.

The different length of the housing fingers promotes a balance of cleaning medium being located between the housing fingers during the cleaning procedure such that the turbidity or dirtying of the cleaning medium determined by means of the optical elements represents the actual turbidity or dirtying. This can be supported by a respective design of the basis and a suitable mounting position of the sensor in a household appliance, respectively.

A further advantage of housing fingers being different long is that the temperature sensor can be arranged further into the cleaning medium without essentially enlarging the design of the sensor.

Preferably, the temperature sensor is surrounded by a heat conduction paste or a gel, which can fill out the end portion of the second housing finger comprising the temperature sensor. The heat conduction paste provides for an improved heat transfer from the cleaning medium external to the housing via the housing, more precisely the material of the second housing finger, to the temperature sensor. Further, in this manner, the temperature sensor is not rigidly/firmly cast in the housing whereby problems due to different temperature co-efficients of the housing and the materials surrounding the temperature sensor are avoided. Furthermore, the material surrounding the temperature sensor is not brittle and provides for a better adhesion to the housing compared to rigid cast substances.

The utilization of a heat conduction paste for improving the temperature transfer to the temperature sensor allows a more simple design of the sensor since the heat conduction paste is only required to be injected or filled into the end portion of the second housing finger. This can take place prior or after arranging the temperature sensor.

Further, a separation means can be employed which separates the end portion of the second housing finger from the remaining portions of the sensor being enclosed by the housing. Preferably, the separation means provides for a seal, at least sealing with respect to the heat conduction paste, for the end portion of the second housing finger.

In dependence from the application of the sensor, for example in dependence from its orientation in a washing machine or a dishwasher, the separation means can be designed such that it prevents a flowing of the heat conduction paste out of the second housing finer. Alternatively or in addition, the separation means can also provide for a thermal insolation or separation of the portion of the second housing finger comprising the temperature sensor from the portion comprising the second optical element.

For arranging the optical elements and the temperature sensor in the housing, it is contemplated to employ a support being connected to these components, which is, for an assembly of the sensor, introduced into the housing and mounted therein, for example by means of clamp, snap and/or adhesive connections. Also, the support can provide for a positioning and orientation, respectively, of the optical elements and/or the temperature sensor in the housing.

In an advantageous manner, the separation means is provided by the support, for example by means of a flat structure being formed on the support which seals, comparable to a lid, the end portion of the second, longer housing finger.

Further, it is contemplated to connect the optical elements and the temperature sensor with a circuit board such that the electrical components of the sensor according to the invention can be arranged therein in a pre-manufactured manner.

The support for the optical elements and the temperature sensor can be connected with the circuit board or can be integrally incorporated. Further, it is possible that the function of the support is provided by the circuit board itself. The latter case also applies for the separation means which can be provided, for example, by means of a surface which essentially extends perpendicular to the actual circuit board.

Preferably, the circuit board comprises a plug connector extending from the housing in order to operatively connect the sensor with a washing machine or a dishwasher in a simple manner.

By means of a lid, the space enclosed by the housing can be sealed in order to, for example, prevent a penetration of undesired substances (i.e. drifting cleaning medium and dirt). Furthermore, the lid can be formed such that the plug connector of the circuit board is extending through the lid to the outside.

Moreover, the lid can have a shape which surrounds, comparable to a plug housing, the part of the plug connector which extends to the outside. In this manner, the lid can serve as a form fit connection to a washing machine or a dishwasher, wherein structures contemplated for the respective portions of the lid can provide for a coding for connecting the sensor with a washing machine or a dishwasher and/or for a snap or click connection.

SHORT DESCRIPTION OF THE DRAWINGS

Figure 2:
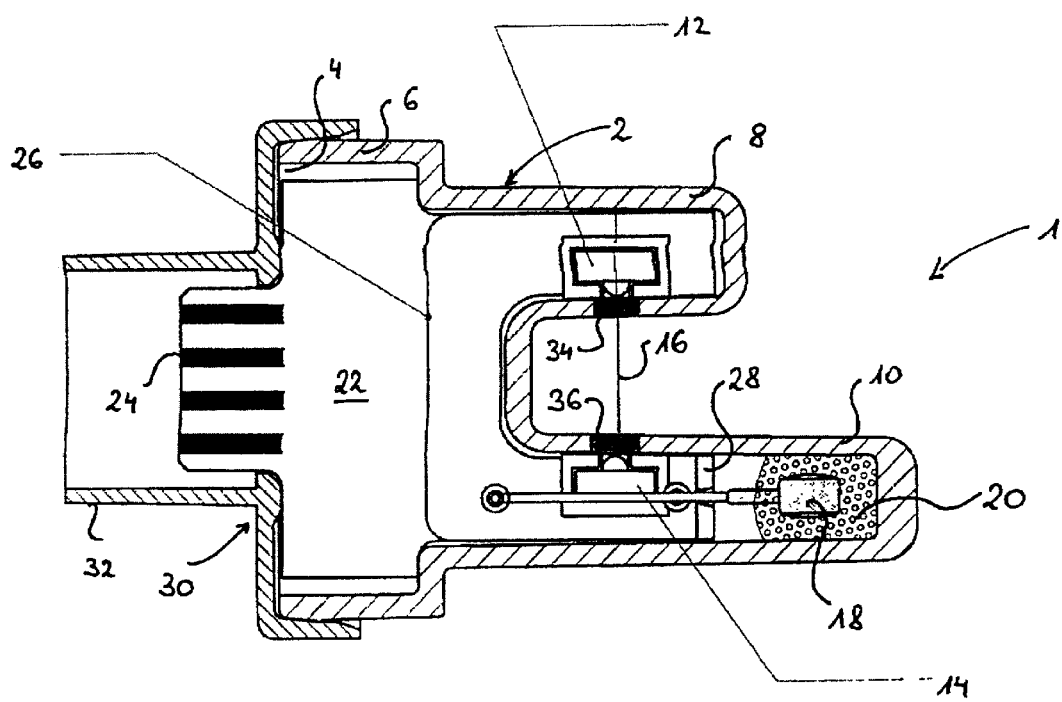

In the following description of preferred embodiments it is referred to the enclosed drawings which show:

FIGS. 1 and 2 schematic cross-sectional views of a sensor according to the invention.

DESCRIPTION OF PREFERRED EMBODIMENTS

FIGS. 1 and 2 show schematic cross-sectional views of a sensor for household appliances, in particular washing machines and dishwashers, for sensing of the turbidity and the temperature of a cleaning medium, for example water, cleaning fluids, vapours, etc. and combinations thereof.

The sensor in generally being designated with 1 comprises a housing 2 with an opening 4 surrounded by a basis 6. Further, the housing 2 comprises two ends 8 and 10 which extend, comparable to fingers, from the basis. As can be seen in FIG. 2, these ends 8 and 10 of the housing 2, which are shortly referred to as fingers in the following, are different long in order to, as explained in the following, to allow for an improved temperature sensing.

For a sensing of the turbidity, optical elements 12 and 14 are arranged in the housing 2, each in one of the fingers 8 and 10, opposing each other. Interactions of a sensing beam propagating between the optical elements 12 and 14 with a cleaning medium located between the fingers 8 and 10 (i.e. external to the housing 2) are employed to determine the turbidity or dirtying of the cleaning medium. In dependence from the parameter(s) to be sensed for the cleaning medium which indicate(s) the turbidity, dirtying and the like of the cleaning medium, for example with dirt particles, suspended matter, fabric rests, etc., the sensing beam 16 can be an optical and/or acoustical sensing beam. For example, in order to separately measure the turbidity/dirtying of the cleaning medium by dirt particles on one hand, and by forming of foam on the other hand, it is possible for an application of an optical sensing beam to vary its frequency, preferably in an alternate manner, such that the parameters corresponding to the effects leading to the different turbidity/dirtying are generated.

For a generation of the sensing beam 16, the optical elements 12 and 14 can comprise a sender and a receiver, respectively. Further, it is contemplated that one of the optical elements 12 and 14 comprises a sender and a receiver being integrally incorporated, while the other optical element comprises means for returning the transmitted light beam to the other optical element. For the sake of simplicity, in the following it is assumed that the optical element 12 operates as sender, while the optical element 14 is utilized as receiver.

In the longer finger 10 which is extending further into the cleaning medium in the case of an arrangement of the sensor 1 in a washing machine or a dishwasher a temperature sensor 18 is arranged. In particular, the temperature sensor 18 is arranged in the finger 10 in its outer, i.e. the basis 6 opposing end. Due to the finger 10 further extending into the cleaning medium, the response time of the temperature sensor 18 with respect to the temperature changes of the cleaning medium is improved. Further, more precise temperature measurements are possible since the temperature sensor 18 is remotely located from the remaining components of the sensor 1 and, accordingly, heat generations and/or changes in the sensor 1 do not or only in essentially effect temperature measurements.

Furthermore, the end portion of the finger 10, wherein the temperature sensor 18 is located, is, at least partially, filled with heat conduction paste or a gel 20 such that the temperature sensor, more particular its temperature sensitive components, are surrounded by the heat conduction paste 20. The heat conduction paste 20 increases the heat contact of the temperature sensor 18 with portion of the finger 10 surrounding the same and, thereby, also the heat contact of the temperature sensor 18 with the cleaning medium. As an alternative or in addition, the temperature sensor 18 can be arranged in the finger 10 such that the temperature sensor 18 and its temperature sensitive components, respectively, directly contact the finger 10.

For control, for operation and for energy supply, the optical elements 12 and 14 and the temperature sensor 18 are connected with a circuit board 22 by means of electrical lines (not designated). The circuit board 22 comprises, on its end opposing the fingers 8 and 10, a plug connector 24 which extends through the opening 4.

For supporting the optical elements 12 and 14 and the temperature sensor 18, a support 28 mounted to the circuit board 22 is provided which also serves for arranging the circuit board 22 and of the optical elements 12 and 14 and the temperature sensor 18, respectively, in the housing 2. In particular, the support 26 comprises a surface 28 essentially extending perpendicular to the circuit board 22 which seals the end portion of the finger 10 wherein the temperature sensor 18 is located in a manner comparable to a lid. This abutment of the end portion of the finger 10 provides for a thermal separation of the temperature sensor 18 from the remaining portions of the sensor 1 and, in particular, from the in general heat generating members coupled to the circuit board 22. Furthermore, the surface 28, which is also designated as lid in the following, avoids a flowing of the heat conduction paste 20 (in case utilized) out of the end portion of the finger 10.

In dependence of the design of the circuit board 22, it is possible to leave out the support 26 if its functions are provided by the circuit board 22. In particular, in this case, the circuit board 22 should comprise a structure or surface which, comparable to the lid 28, (in an advantageous manner thermally) separates the end portion of the finger 10 from the remaining portions on the sensor 1 being enclosed by the housing 2 and, in case required, closes the same in a sealing manner. Further, the lid 28 can be provided by an electric or electronic member having a respective shape being arranged on the circuit board 22.

The open end 4 of the housing 2 is essentially sealed with a housing lid 30. The housing lid 30 can be connected with the housing 2 by means of click and/or snap connections in order to allow for a simply assembly of the sensor 1. In order to avoid a penetration of the cleaning medium into the interior of the sensor 1, the portions wherein the housing lid 30 contacts the housing 2, sealing elements (not shown) can be employed, in particular in the case the connection of the housing lid 30 and the housing 2 itself does not ensure a proper sealing of the sensor 1.

The housing lid 30 comprises an opening (not designated) through which the plug connector 24 of the circuit board 22 is extending wherein a sealing can be also carried out. Further, the housing lid 30 comprises a wall 32 at least partially surrounding the plug connector 24 which serves as guide and connection with corresponding structures and/or components of a household appliance, such as a washing machine or a dishwasher. The wall 32 allows, for example, to plug in the sensor 1 into a correspondingly shaped opening or recess in the interior of a household appliance in order to connect the plug connector 24 with corresponding electric components.

In dependence of the employed optical elements 12 and 14, in particular in dependence of the employed sensing beam 16, it is contemplated that the housing 2 is translucent for the sensing beam 16 at least in the portions wherein the optical elements 12 and 14 are arranged. In this manner, for example, the housing 2 can include, as indicated in FIG. 2, translucent portions or windows 34 and 36 in the case the sensing beam 16 is an optical sensing beam. A simplification can be obtained if the housing 2 as a whole is made from a material been translucent for the measurement beam 16, for example made from Perspex.

Furthermore, it is contemplated that the housing 2 comprises, at least in the reception end of the finger 10 wherein this temperature sensor 18 is arranged, a material the thermal properties of which allow a fast and correct sensing of a temperature of the cleaning medium external of the housing 2 by means of the temperature sensor 18 been located inside. In an advantageous manner, the housing 2 is made from a material which is both translucent for the sensing beam 16 and provides for an optimized heat transfer to the temperature sensor 18.

What is claimed is:

1. Sensor for washing machines and dishwashers, comprising:
   a housing (2) which comprises a basis (6) and first and second housing fingers (8, 10) extending from the basis (6),
   a first optical element (12), which is arranged in the first housing finger (8) spaced apart from the basis (6),
   a second optical element (14), which is arranged in the second housing finger (10) spaced apart from the basis (6), wherein a sensing beam (16) being transmitted and received by the optical elements (12, 14) propagates between the housing fingers (18, 10) exterior to the housing (2) for sensing the turbidity of a cleaning medium at least partially surrounding the housing (2), and
   a temperature sensor (18) which is arranged, for sensing the temperature of the cleaning medium, in the second housing finger (10) in a greater distance from the basis (6) compared to the second optical element (14).

2. Sensor according to claim 1, wherein the first and second housing fingers (8, 10) are essentially extending parallel with respect to each other.

3. Sensor according to claim 1 or 2, wherein the first housing finger (8) is shorter than the second housing finger (10).

4. Sensor according to claim 1, wherein the first optical element (12) is arranged in an end portion of the first housing finger (8).

5. Sensor according to claim 1, wherein the second optical element (14) is arranged, opposite the first optical element (12), in the second housing finger (10) in a portion between the temperature sensor (18) and the basis (6).

6. Sensor according to claim 1, wherein the temperature sensor (18) is surrounded by a heat conduction paste (20) or a gel (20) which substantially completely fills the portion of the second housing finger (10) comprising the temperature sensor (18).

7. Sensor according to claim 1, wherein the portion of the second housing finger (10) comprising the temperature sensor (18) is separated by a separation means (28) from the remaining portions being enclosed by the housing (2).

8. Sensor according to claim 7, wherein the separation means (28) closes the portion of the second housing finger (10) comprising the temperature sensor (18) in a sealing manner.

9. Sensor according to claim 1, wherein the optical elements (12, 14) and the temperature sensor (18) are arranged in the housing (2) by means of a support (26).

10. Sensor according to claim 9, wherein the portion of the second housing finger (10) comprising the temperature sensor (18) is separated by a separation means (28) from the remaining portions being enclosed by the housing (2), the separation means (28) being an essentially plane structure of the support (26).

11. Sensor according to claim 1, wherein the optical elements (12, 14) and the temperature sensor (1 8)are connected by a circuit board (22) been arranged in the housing (2) in an electrically conductive manner.

12. Sensor according to claim 11, wherein the portion of the second housing finger (10) comprising the temperature sensor (18) is separated by a separation means (28) from the remaining portions being enclosed by the housing (2), the separation means (28) being a plane structure which is essentially extending perpendicular to the circuit board (22).

13. Sensor according to claim 11, wherein the portion of the second housing finger (10) comprising the temperature sensor (18) is separated by a separation means (28) from the remaining portions being enclosed by the housing (2), the separation means (28) being provided by the circuit board (22) or by means of a member arranged thereon.

14. Sensor according to claim 11, wherein the optical elements (12, 14) and the temperature sensor (18) are arranged in the housing (2) by means of a support (26), the support (26) being connected to the circuit board (22).

15. Sensor according to claim 11, wherein the circuit board (22) comprises a plug connector (24) extending from the housing (2) for electrically connecting to a household appliance.

16. Sensor according to claim 1, wherein the housing (2) comprises a housing lid (30) being opposite the housing fingers (8, 10) wherein the housing (2) and the housing lid (30) define a sensor interior.

17. Sensor according to claim 16, wherein a plug connector (24) of a circuit board (22) being arranged in the housing (2) is extending from the sensor interior through the housing lid (30), the optical elements (12, 14) and the temperature sensor (18) being connected to the circuit board (22) in an electrically conductive manner.

18. Housing for a sensor for washing machines and dishwashers, comprising:
    a basis (6),
    a first housing finger (8) extending from the basis (6) for receiving a first optical element (12) in a portion of the first housing finger (8) spaced apart from the basis (6), and
    a second housing finger (10) extending from the basis (6) for receiving a second optical element (14) in a portion of the first housing finger (8) spaced apart from the basis (6), wherein the first and second optical elements (12) are provided for sensing the turbidity of a cleaning medium at least partially surrounding the housing by means of a sensing beam (16) propagating between the first and second optical elements (12,14) and for receiving a temperature sensor (18) for sensing the temperature of the cleaning medium, wherein the portion of the second housing finger (8) provided for receiving the temperature sensor (18) is located in a greater distance from the basis (6) compared to the portion of the second housing finger (8) provided for receiving the second optical element (14).

19. Housing according to claim 18, wherein the first and the second housing fingers (8, 10) are extending essentially parallel with respect to each other.

20. Housing according to claim 18 or 19, wherein the first housing finger (8) is shorter than the second housing finger (10).

21. Housing according to claim 18, wherein the portion being provided for arranging the first optical element (12) is located in an end portion of the first housing finger (8).

22. Housing according to claim 18, wherein the portion of the second housing finger (10) being provided for arranging the second optical element (14) is located opposite to the portion of the first housing finger (8) being provided for arranging the first optical element (12) in a portion between the portion of the second housing finger (10) being provided for arranging the temperature sensor (18) and the basis (6).

23. Housing according to claim 18, wherein a separation means (28) is provided in order to separate the portion of the second housing finger (10) being provided for arranging the temperature sensor (18) from the remaining portions being enclosed by the housing.

24. Housing according to claim 18, wherein a support (26) to be arranged in the housing (2) is provided for arranging the optical elements (12, 14) and/or the temperature sensor (18).

25. Housing according to claim 24, wherein a separation means (28) is provided in order to separate the portion of the second housing finger (10) being provided for arranging the temperature sensor (18) from the remaining portions being enclosed by the housing, the separation means (28) being an essentially plane structure of the support (26).

26. Housing according to claim 18, wherein a circuit board (22) to be arranged in the housing is provided for electrically connecting the optical elements (12, 14) and/or the temperature sensor (18).

27. Housing according to claim 26, wherein a separation means (28) is provided in order to separate the portion of the second housing finger (10) being provided for arranging the temperature sensor (18) from the remaining portions being enclosed by the housing, the separation means (28) being a plane structure which is essentially perpendicular extending with respect to the circuit board (22).

28. Housing according to claim 26, wherein a separation means (28) is provided in order to separate the portion of the second housing finger (10) being provided for arranging the temperature sensor (18) from the remaining portions being enclosed by the housing, the separation means (28) being provided by the circuit board (22) or by a member arranged thereon.

29. Housing according to claim 26, wherein a support (26) to be arranged in the housing (2) is provided for arranging the optical elements (12, 14) and/or the temperature sensor (18), the support (26) being provided for connecting to the circuit board (22).

30. Housing according to claim 26, wherein the circuit board (22) comprises a plug connector (24) extending from the housing for electrically connecting to a household appliance.

31. Housing according to claim 18, comprising a housing lid (30) to be arranged opposite the housing fingers (8, 10) wherein the housing and the housing lid (30) define a sensor interior.

32. Housing according to claim 31, wherein a plug connector (24) of a circuit board (22) being arranged in the housing (2) is extending from the sensor interior through the housing lid (30), the optical elements (12, 14) and the temperature sensor (18) being connected to the circuit board (22) in an electrically conductive manner.

* * * * *